United States Patent [19]

Severns

[11] Patent Number: 5,297,559
[45] Date of Patent: Mar. 29, 1994

[54] APPARATUS FOR TESTING COLOR VISION

[75] Inventor: Matthew L. Severns, McLean, Va.

[73] Assignee: LKC Technologies, Inc., Gaithersburg, Md.

[21] Appl. No.: 959,797

[22] Filed: Oct. 13, 1992

[51] Int. Cl.[5] .............................................. A61B 13/00
[52] U.S. Cl. .................................... 128/745; 351/242; 351/243
[58] Field of Search .................... 128/745, 395, 396; 351/242, 243, 244, 237

[56] References Cited

U.S. PATENT DOCUMENTS

| | | | |
|---|---|---|---|
| 3,807,838 | 4/1974 | Meyers | 351/242 |
| 3,947,099 | 3/1976 | Grohlman et al. | 351/242 |
| 4,285,580 | 8/1981 | Murr | 351/35 |
| 4,324,460 | 4/1982 | Daley | 351/242 |
| 4,765,731 | 8/1988 | Williams | 351/243 |
| 4,784,483 | 11/1988 | Holladay et al. | 351/243 |
| 4,848,898 | 7/1989 | Massof | 351/242 |
| 4,966,453 | 10/1990 | Chang et al. | 351/242 |

FOREIGN PATENT DOCUMENTS 2602304  7/1977  Fed. Rep. of Germany ...... 351/242

Primary Examiner—Stephen C. Pellegrino
Assistant Examiner—Guy V. Tucker
Attorney, Agent, or Firm—Pollock, VandeSande & Priddy

[57] ABSTRACT

An opaque plate is positioned in front of a patient undergoing color vision testing. A number of openings are formed in the plate. Behind each disk is a hollow sphere having colored light sources mounted therein. By selectively energizing the colored light sources in a sphere, a mixture of light is presented at the corresponding transparent disk at a selected intensity. A tester can select one or more spheres to be internally illuminated by color light sources so that the patient is presented with a pattern of selectable color mixtures which checks his color vision.

8 Claims, 4 Drawing Sheets

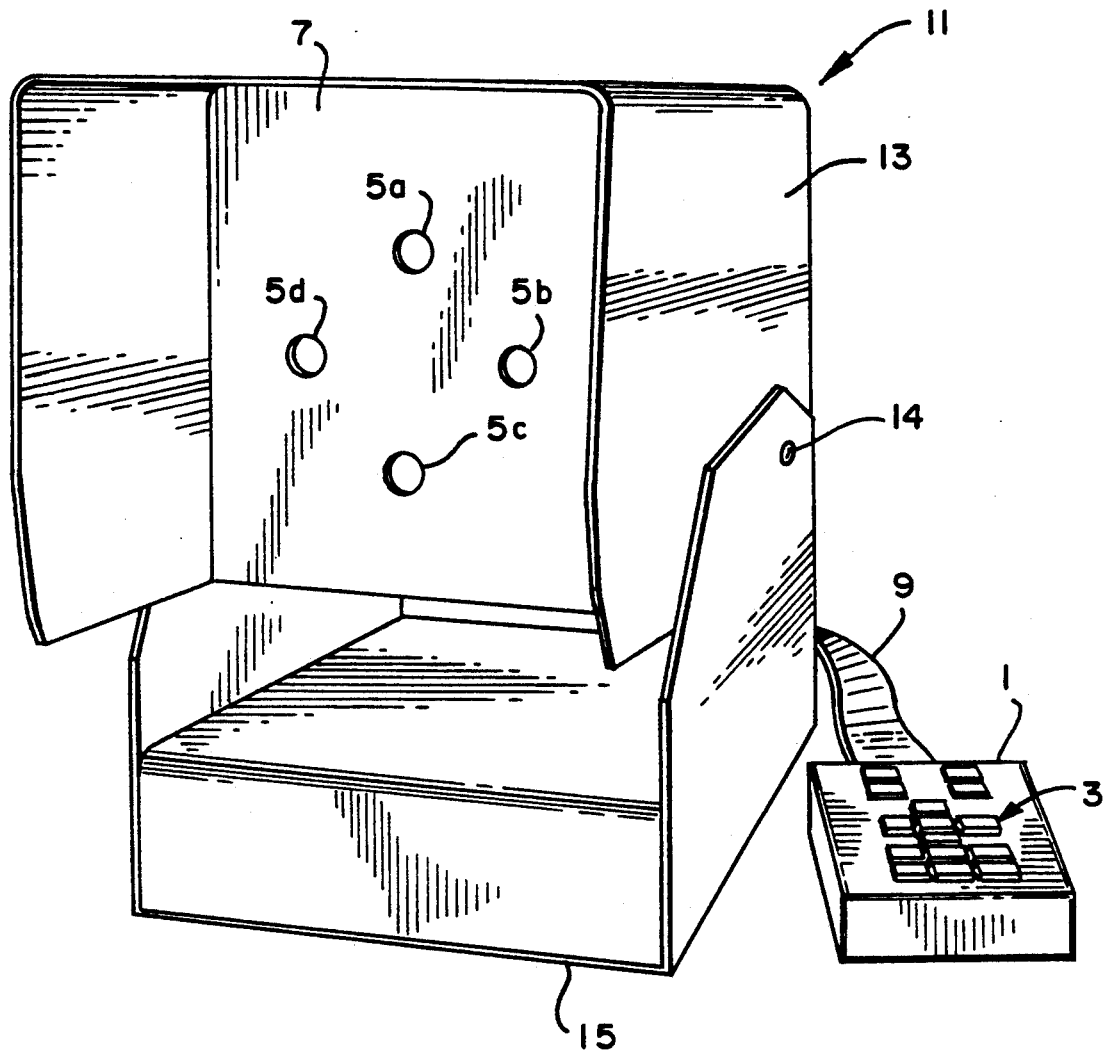
FIG_1

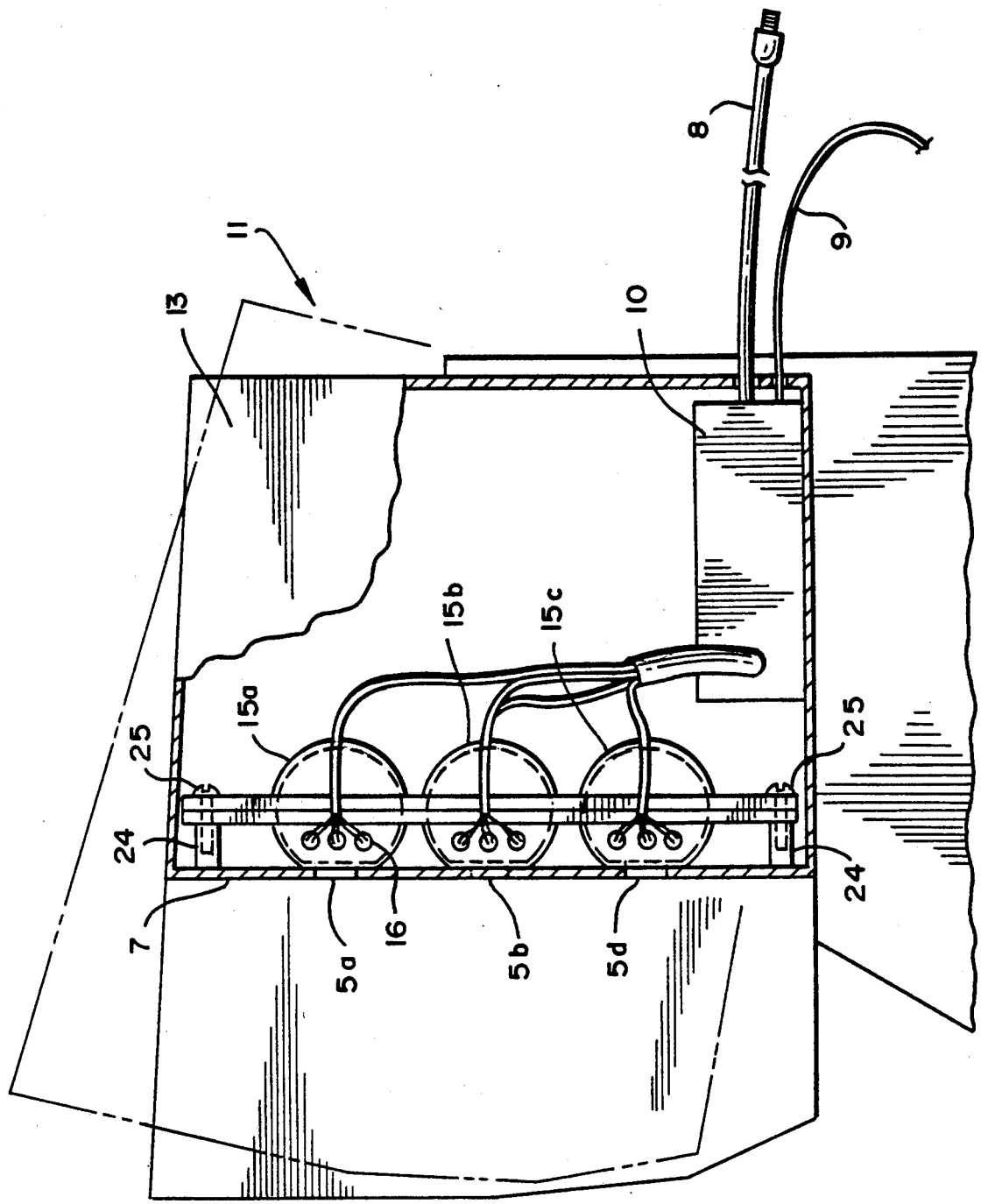

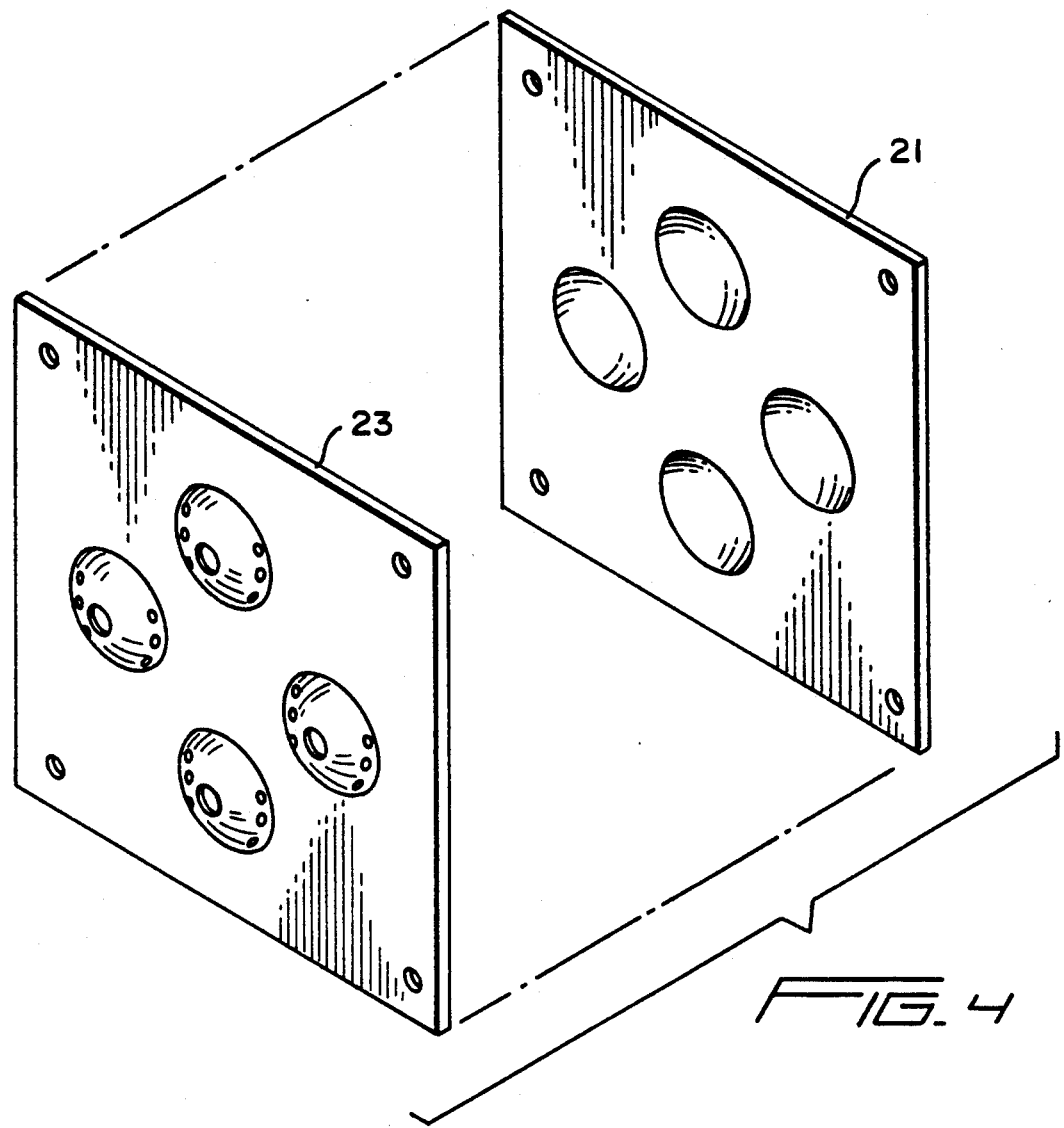
FIG. 4
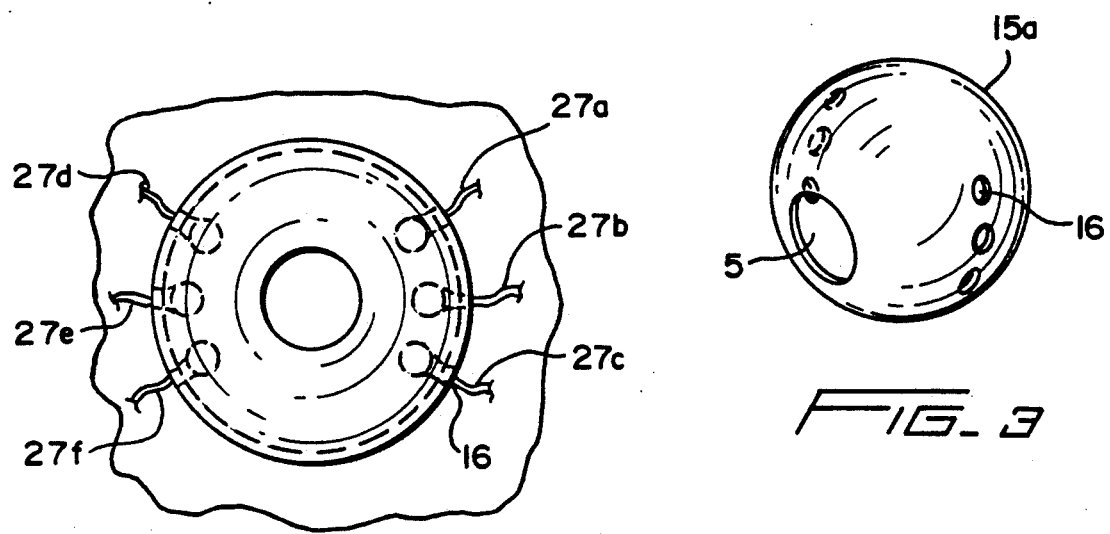
FIG. 5
FIG. 3

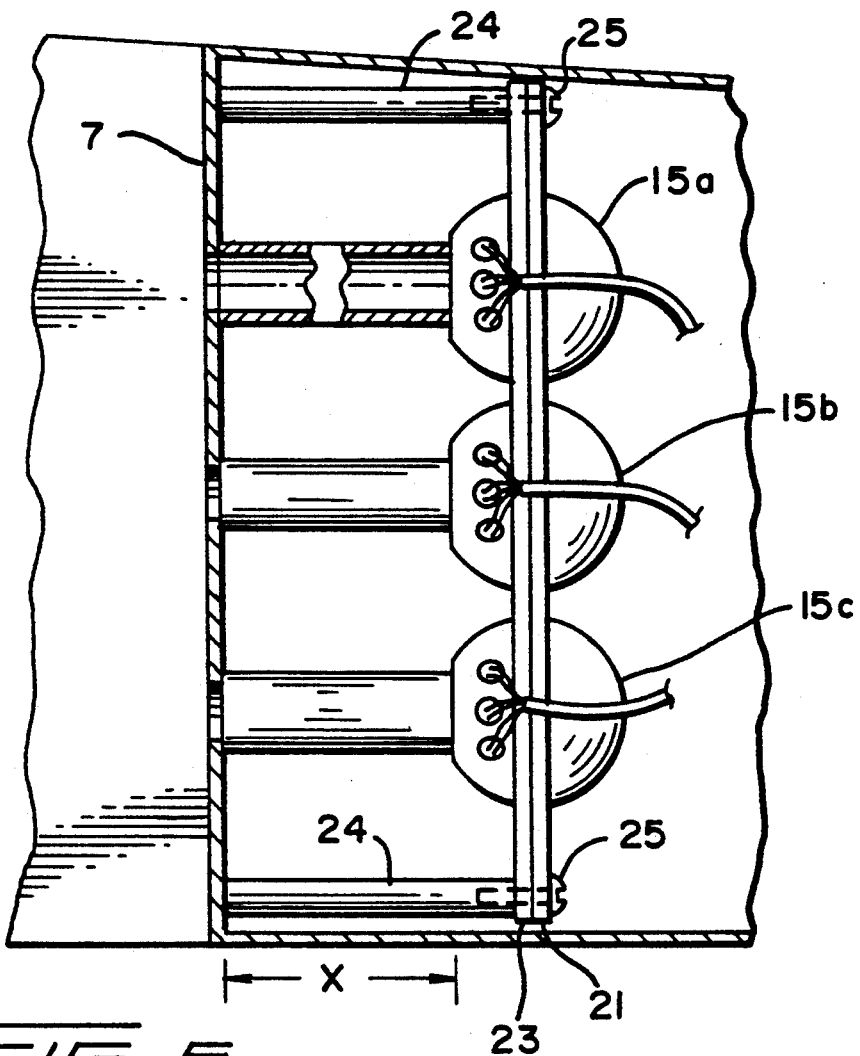

APPARATUS FOR TESTING COLOR VISION

FIELD OF THE INVENTION

This invention relates to color vision testers, and more particularly to a tester which can easily identify the type and degree of color deficiency, if any, which a patient has.

BACKGROUND OF THE INVENTION

As is well known, the human visual system is trichromatic. All colors can be matched by a mixture of three primary colors, namely red, green and blue. This trichromatic property of human color vision is a consequence of three different photoreceptor types in the retina: the R receptor (maximally sensitive to the red end of the spectrum), the G receptor (maximally sensitive to the middle, or green part of the spectrum), and the B receptor (maximally sensitive to the blue end of the spectrum). The ratios of red, green and blue primaries in a color mixture that is made to match some arbitrary color are determined by the spectral absorption of the characteristics of the photo pigments in the three types of receptors.

Approximately 8% of males and 0.2% of females have abnormal color vision due to a defect inherent in the X-chromosome. One form of color vision defect, called anomalous trichromacy, is characterized by abnormal spectral absorption characteristics of the R receptor photopigment (protanomalous trichromat) or of the G receptor photopigment (deuteranomalous trichromat). Anomalous trichromats still require three primary colors in a mixture to perform color matching. However, the ratio of the primaries is anomalous in comparison to the normal population. A second form of color vision defect, called dichromacy, is characterized by an absence of the R receptor photopigment (protanope) or an absence of the G receptor photopigment (deuteranope). Protanope and deuteranope require only two primary colors and a mixture to perform color matching.

X-linked color vision defects are diagnosed on the basis of tests that are standardized against color matching. In particular, a yellow lamp is matched by normal trichromats with a unique mixture of a red primary and a green primary. Relative to the normal match, protanomalous trichromats add too much red to the mixture and deuteranomalous trichromats add too much green to the mixture. Protanope and deuteranope match the red alone to the yellow, green alone to the yellow, and any ratio of red to green in a mixture to the yellow. The major difference between protanope and deuteranope is in the sensitivity thereof to colored lamps. Protanopes are very insensitive to red light, consequently red lamps appear much dimmer than do yellow or green lamps that look to be the same brightness for normals. Deuteranopes have the same sensitivity to colors as does the normal.

In addition to inherited red-green color vision deficiencies, some people suffer from losses in the ability to discriminate blue from yellow. These losses are most frequently caused by disease processes such as diabetes mellitus or glaucoma, but may also be caused by the normal yellowing of the lens of the eye with age. Blue-yellow defects are also diagnosed on the basis of tests that are standardized against color matching. In these tests, there is somewhat more variety than in the red-green tests. The most common tests are: a mixture of blue-violet and green are matched against a mixture of blue and yellow lights (the Moreland equation), a mixture of blue and yellow are matched against a white light (the Pickford-Lakowski equation), or a mixture of blue-violet and green are matched against a blue-green light (the Engelking-Trendelenberg equation).

A variety of methods and instruments are used to test the above discussed color vision deficiencies of a patient. One of the more common methods involves the use of pseudoisochromatic plates. These plates comprise a series of dots of different hues of color printed on a heavy white paper board. By mixing certain colors, specific dots can be varied in color to form patterns which can be, for example, in the form of a numeral or a letter. A normal patient shown a particular card and asked to identify the pattern of the different colored dots could readily do so whereas a patient with a color deficiency would identify all dots as being the same color thereby being unable to recognize the numeral or letter.

Pseudoisochromatic plates are widely used; however, they have certain drawbacks which prevent an accurate accounting of a patient's deficiency. For example, the color hues on pseudoisochromatic plates are not calibrated. Thus, although the plates are very easy to use since the patient being observed only needs to look at the various different plates and inform the clinician when he sees a figure, the plates do not have precision in terms of determining the type or degree of color vision a person has. Further, pseudoisochromatic plates require that the patient be capable of pattern recognition; small children (or even adults) can have difficulty recognizing patterns; i.e., numerals or letters formed by dots. In addition, the plates tend to fade over time as they are handled. Any hand oils that are transferred to the cards alter the plate colors over time causing erratic readings.

Finally, the use of pseudoisochromatic plates requires special lighting. To work properly, the cards should be viewed under an illuminant C light (not a fluorescent or incandescent light). Problems arise in that many testers or testing centers have the cards but do not have the proper light; again, this results in inconsistent test results.

A second method commonly used and similar to the pseudoisochromatic plates is the use of slides containing colored dots. These slides work well in combination with acuity charts where a particular patient can have his distance and focus capabilities tested using a common testing apparatus. Slides have a lesser tendency to fade because they are normally handled less. However, slides still require special lighting; and faithful reproduction of the slides is difficult.

A third method of testing color vision deficiency is given in U.S. Pat. No. 3,947,099 to Grolman, et al. Here an anomaloscope that uses a bipartite field having a spectrally pure yellow half and a mixture red and green half for testing the color vision of a patient is disclosed. To perform an anomaloscope test, the patient is instructed to adjust two knobs until the bipartite field appears consistent in color. People who have red-green color deficiencies will either adjust the red-green ratio so that it is totally different from what a person with normal vision would perceive or they may have a lesser color deficiency and simply have a range in which the two halves of the bipartite field appear similar but are in fact different, as perceived by a person with normal color vision. This particular test requires substantial tester/patient interface to determine the range and degree of color deficiency that a patient has.

In addition, this test can be difficult for certain individuals, particularly small children. For instance, in order to adjust the spectral red and green colors of the mixture on one half of a display circle to correspond with the spectral pure yellow color on the other half of the display circle, the patient has to be able to adjust both the ratio of the red and green colors in the mixture and the brightness thereof, in order to look just like the spectral yellow color. There are versions of the anomaloscope that are computer controlled and require less interaction between the patient observer and the tester. However, such versions are expensive when compared to the use of pseudoisochromatic plates. Hence, because the anomaloscope can be difficult for a patient to operate, most clinicians, when testing color vision of a patient, resort to using pseudoisochromatic plates (an example of which is given in Hardy, et al. U.S. Pat. No. 2,937,567).

Another common method of testing for color vision defects, and one that is especially used in testing for blue-yellow color vision defects, is the arrangement test. In this type of test, the patient is presented with an array of colored chips embedded into caps, and is asked "to arrange the caps in order according to color." Misarrangements of the colored caps can be used to deduce color vision defects. Arrangement tests suffer from the same deficiencies as pseudoisochromatic plates, in that they require that the patient understand the task, the colors tend to fade over time as they are handled, hand oils transferred to the color chips will alter the colors over time, and special lighting is required. Additionally, the scoring and interpretation of the test is somewhat complicated.

A fourth method of testing color deficiency of a patient is given by Massof in U.S. Pat. No. 4,848,898. There, an instrument is disclosed which is similar to an anomaloscope but with a multiplicity of lamps. The instrument contains preset values consisting of mild, moderate or severe color deficiencies wherein a patient views a panel of lamps and is asked to pick out a particular light pattern which appears on the screen before him. Depending on the patient's ability to identify the pattern, color deficiencies can be determined within reasonable bounds.

With the Massof invention, it is often difficult for small children (and some adults) to evaluate specific patterns. Although they may recognize that certain lamps appear to be a different color, they cannot actually determine the pattern which exists.

With color vision testing it is important that the test be primarily focused on the fovea and that the field of testing not exceed 1½-2 degrees of center. Large screen tests wherein a number of discriminating light sources are available to the patient, although he has a strong deficiency in the central focus area, i.e., the fovea, can result in some pattern recognition because of the large vision field while in fact the patient suffers some color deficiency. Also, the Massof instrument is limited to testing red-green color deficiencies.

Therefore, there exists a need for an instrument that can provide for both easy operation and classification of a patient's color vision defect.

BRIEF DESCRIPTION OF THE PRESENT INVENTION

It is an object of the present invention to provide a color testing apparatus that is relatively easy to use and is not hampered by the problems of prior color vision testing apparatus. Specifically, the present invention does not require special lighting (other than to be displayed in a dim environment), nor does it require the recognition of patterns or extensive tester/patient interaction.

It is another object of the present invention to fulfill the above stated needs by utilizing a plurality of light sources, specifically yellow, red, green, blue and white light sources which can be mixed in spheres behind the viewing screen and presented to a patient as a flat uniform colored area within an opaque background. The tester varies both the color and intensity of the individual light sources with some computer (or other electronic) assistance to adequately determine a patient's deficiencies.

The present invention, without any action on the part of the patient being observed, other than acknowledging whether a specific lighted area as seen on the screen is different in color than the other colored lighted areas presented, provides an easy-to-use device which can also accurately measure the type of color vision deficiencies that a patient has.

Furthermore, the present invention is able to minimize cheating by the patient being tested since the tester can readily select different areas to present different colors; the patient merely has to indicate which color area appears different, i.e., top, bottom, left or right.

BRIEF DESCRIPTION OF THE FIGURES

The above-mentioned objects and advantages of the present invention will be more clearly understood when considered in conjunction with the accompanying drawings, in which:

FIG. 1 is a plan view of the present invention showing the observation panel and tester control box;

FIG. 2 is a side view in partial cross section of the present invention showing three of the four light-mixing spheres;

FIG. 3 is a plan view of one of the spheres showing both a patient viewing port and six light access apertures;

FIG. 4 is a plan view of one embodiment of the present invention wherein the spheres comprise two plates each containing half of the light-mixing spheres;

FIG. 5 is a front view in cross section of a sphere showing the patient viewing port and the six light sources inserted into the sphere;

FIG. 6 is a plan view partially in cross section of a second embodiment of the invention wherein the spheres are displaced at a given distance from the viewing screen.

DETAILED DESCRIPTION OF THE INVENTION

Referring now to FIG. 1, there is shown a plan view of the present invention as it would appear in its patient-ready state. The viewing apparatus, generally designated 11, consists of an opaque background screen 7 preferably dark in color and having a low light reflectance. Appearing on the face of background screen 7 are a plurality of transparent disks. In the preferred embodiment, four transparent disks 5*a, b, c* and *d* are used. The disks are arranged both in number and pattern to be as user friendly as possible. By using a pattern of four disks, as shown in FIG. 1, the patient can identify the disk which appears different in color as top, bottom, left or right. In addition, by using four color disks as opposed to two or three, the probability of a patient guessing the appropriate disk is reduced; this becomes particularly important when working with small children in that they: (1) have an inability to identify letters or numerals and (2) will often guess in the hope of providing the tester with an appropriate answer.

The cover 13 generally conceals the electronics and light sources for providing the red-green, blue-yellow, and blue-green light mixtures shown to the patient through disks 5a, b, c and d. Viewing apparatus 11 in the preferred embodiment is mounted on a conventional platform 15 such that the viewing apparatus can be tilted on axis 14 to provide the best viewing angle to the patient. In operation, a patient is seated in front of the viewing apparatus such that he can readily observe the four colored disks 5a, b, c and d. The tester selects a disk (top, bottom, left or right) to display a different combination of colors than the three remaining disks and then asks the patient to identify the disk that is different in color and/or intensity.

To control the color intensity of the transparent disks 5a, b, c and d, there is a separate key pad generally designated 1. In the preferred embodiment, key pad 1 is connected to viewing apparatus 11 via conventional cable 9. However, the key pad could be mounted directly on platform 15 or cover 13. It should be emphasized that the circuitry in both the key pad 1 and the viewing apparatus 11 are conventionally made from parts which are readily available.

The tester, during operation, uses one of four keys 3 (top, bottom, left, right) located on the key pad 1 to identify a particular disk 5a, b, c or d, which he wishes to have identified as a different color and/or intensity from the other three disks. For example, a tester, while evaluating a red-green or blue-yellow test, may select to have the bottom disk 5c appear different in color and/or intensity to a normal patient. Accordingly, he would select disk 5c from the key pad 1 and would subsequently use a second series of keys 3 to select the color and/or intensity of the red-green or blue-yellow mixtures he wishes to present to the patient. Presumably, the test will be performed in a dimly lit room whereby the color disks 5a, b, c and d, can readily be seen and not interfered with by conventional lighting sources, or alternatively a viewing shield may be utilized, such that the subject places his/her head against a gasket to exclude external light. The shield is of the length to place the subject's eyes at the correct viewing distance from the disks 5a, b, c, and d.

Referring now to FIG. 2, there is shown a side view partially in cross section of viewing apparatus 11. Shown are three of the four spheres 15a, b and c used to mix the colors presented to the patient through patient viewing ports 5 (FIG. 3). The key pad 1, as mentioned above, is connected to the viewing apparatus 11 via cable 9. Conventional power control unit 10 is connected to a voltage source via cable 8 and provides the necessary control circuitry to interface with key pad 1 whereby the tester can select which disk 5a, b, c, or d is to be the test disk and adjust the color and intensity accordingly.

As shown in FIG. 3, each of the spheres 15a, b, c and d, comprises a plurality of small apertures 16 and a viewing port 5. A particular color combination, whether red-green, blue-yellow or blue-green, can be created by mixing the light from the red, green, blue, white and yellow lamps inserted into the sphere. It is not necessary that six different lamps be used in that some light sources combine different color lamps into a single bulb; again, it should be emphasized that such light sources are conventional and readily available. Alternatively, depending on the particular use of the color vision testing apparatus, it may only be necessary to have one or two lamp apertures wherein, for example, a single unit is used to test red-green, blue-green, or blue-yellow.

In the preferred embodiment, it is considered important to use a sphere as opposed to alternate shape configurations. The use of other shapes is conceivable, for example a square; however, such shapes could increase the probability of light becoming trapped in corners or cavities thereby interfering with the intensity and thus the color observed by the patient. In addition, improperly shaped mixing cavities can create hot spots which might enable an abnormal patient to identify the different colored light disk.

As shown in FIG. 5, lamps 27a, b, c, d, e and f, are inserted through lamp apertures 16. These lamps can be red, green, blue, white and/or yellow lamps. Each sphere should be capable of mixing colors to test red-green and/or blue-yellow color deficiencies. Further, it is important that the lamps 27a, b, c, d, e and f, be out of the field of vision as seen through transparent disks 5a, b, c and d. If the lamps are within the field of view, hot spots can again be created thereby cuing the patient as to the different colored disk. Alternatively, as can be seen in FIG. 4, lamp access apertures should be configured such that the highest intensity portions of the lamps 27a, b, c, d, and e are directed away from transparent disks 5a, b, c and d. This is best accomplished by placing the lamp apertures on the same hemisphere as viewing port 5.

In a preferred embodiment of the invention, the spheres 15a, b, c and d are created by using a clamshell plate configuration wherein each plate contains ½ of the sphere 15a, b, c and d; this is shown in FIG. 4. When the two plates 21, 23 are combined they complete four spheres. This is beneficial in that a divided sphere is easier to work with when installing the individual light sources 27a, b, c, d, e and f. As shown in FIG. 2, plates 21 and 23 are secured to opaque background screen using dowels 24 and screws 25.

FIG. 6 shows a second embodiment of the present invention wherein the spheres 15a, b and c are located at distance X away from opaque background screen 7. This embodiment enhances light mixing characteristics and therefore reduces hot spots as compared to the embodiment of FIG. 2. The light mixing spheres 15a, b, c and d as shown in FIG. 2 are very close to background screen 7 which in turn places lamps 27a, b, c, d, e and f close to background screen 7 as well. By placing the sphere a distance X from background screen 7, lamps 27a, b, c, d, e and f are also moved away from background screen 7, thereby reducing the probability that the patient will notice hot spots created by lamps 27a, b, c, d, e and f in close proximity to the patient.

It should be understood that the invention is not limited to the exact details of construction shown and described herein for obvious modifications will occur to persons skilled in the art.

I claim:

1. An apparatus for evaluating color vision of a subject comprising:
   a planar background panel;
   a plurality of viewing ports formed in said background panel;
   a hollow light reflective sperical member located behind each of said viewing ports, each hollow member having an opening in optical alignment with one of said viewing ports;
   a plurality of side apertures formed in each hollow member, each of said apertures receiving a respective lamp therethrough for selectively shining a differently colored light against an interior surface of said hollow member for mixing with other colored lights upon reflection from said interior surface;
   switch means for simultaneously and selectively energizing the lamps in said hollow members; and
   means for simultaneously controlling the luminance of light emitted from the selected lamps.

2. The apparatus set forth in claim 1 wherein the apparatus further includes a keyboard for mounting said switch means and said controlling means thereon.

3. The apparatus set forth in claim 1 wherein each lamp passes through a circumference of a vertical plane intersecting said hollow member, and is out of the line of sight of said subject undergoing testing.

4. The apparatus set forth in claim 1 wherein said hollow members are comprised of two halves, said halves formed in two correspondingly positioned mating plates, and further wherein means are provided for securing said plates together to complete formation of said hollow members.

5. The apparatus set forth in claim 1 wherein the opening in said hollow members is connected to a respective view port by a tubular member for extending the optical path between said opening and a respective view port thus causing more extensive color mixing of said lamp light colors upon their reflection from said internal surface of each of said hollow members.

6. An apparatus for evaluating color vision of a subject comprising:
   a dark planar background panel;
   a plurality of viewing ports formed in said background panel;
   a hollow light reflecting spherical member located behind each respective viewing port, each spherical member having an opening in optical alignment with one of said viewing ports;
   a plurality of apertures formed along a circumference of each spherical member, each aperture receiving a respective lamp therethrough for selectively shining a differently colored light against the interior surface of the spherical member for mixing with other colored lights upon reflection from the surface;
   each lamp passing through a circumference of a non-equatorial vertical plane intersecting said hollow member in a forward hemisphere, and is out of the line of sight of said subject undergoing testing; and
   a keyboard including:
   (a) switch means for selectively and simultaneously energizing the lamps in the spherical members; and
   (b) means for simultaneously controlling the luminance of light emitted from the selected lamps.

7. The apparatus set forth in claim 6 wherein said spherical members are comprised of mating hemispherical members formed in two correspondingly positioned mating plates, and further wherein means are provided for securing said plates together to complete formation of said spherical members.

8. The apparatus set forth in claim 6 wherein each opening in the spherical members is connected to a respective viewing port by a tubular member for extending the optical path between said opening and a respective viewing port thus causing more extensive color mixing of the lamp light colors upon their reflection from the internal surface of said spherical members.

* * * * *